United States Patent [19]
Beach et al.

[11] Patent Number: 5,695,950
[45] Date of Patent: *Dec. 9, 1997

[54] METHOD OF SCREENING FOR ANTIMITOTIC COMPOUNDS USING THE CDC25 TYROSINE PHOSPHATASE

[75] Inventors: David H. Beach, Huntington Bay; Konstantin Galaktionov, Cold Spring Harbor, both of N.Y.

[73] Assignee: Cold Spring Harbor Laboratory, Cold Spring Harbor, N.Y.

[*] Notice: The team of this patent shall not extend beyond the expiration date of Pat. No. 5,294,538.

[21] Appl. No.: 189,206

[22] Filed: Jan. 31, 1994

Related U.S. Application Data

[63] Continuation of Ser. No. 878,640, May 5, 1992, Pat. No. 5,294,538, which is a continuation-in-part of Ser. No. 793,601, Nov. 18, 1991, abandoned.

[51] Int. Cl.$^6$ ............................ C12Q 1/42; C12P 21/06; C12N 1/20; C12N 15/00
[52] U.S. Cl. .................. 435/21; 435/69.1; 435/69.3; 435/69.7; 435/172.3; 435/193; 435/194; 435/252.3; 435/320.1; 514/44; 536/22.1; 536/23.1; 536/23.2; 536/23.5
[58] Field of Search ................. 435/21, 69.1, 69.3, 435/69.7, 172.3, 193, 194, 320.1, 252.3; 514/44; 536/22.1, 23.1, 23.2, 23.5

[56] References Cited

U.S. PATENT DOCUMENTS

| | | | |
|---|---|---|---|
| 5,262,409 | 11/1993 | Margolis et al. | 514/183 |
| 5,294,538 | 3/1994 | Beach | 435/21 |

OTHER PUBLICATIONS

Baratte et al., "Screening for Antimitotic Compounds Using the cdc25 Tyrosine Phosphatase, an Activator of the Mitosis–inducing p34$^{cdc2}$/cyclinB$^{cdc13}$ Protein Kinase", *Anticancer Research* 12: 873–880 (1992).

Camonis et al., "Characterization, Cloning and Sequence Analysis of the cdc25 Gene which Controls the Cyclic AMP level of Saccharomyces Cerevisiae", *Embo J* 5: 375–380 (1986).

Daniel et al., "Clones from Two Different Genomic Regions Complement the cdc25 Start Mutation of Saccharomyces", *Curr Genet* 10 643–646 (1986).

Daniel, "The cdc25 Start Gene of Saccharomyces Cerevisiae: Sequencing of the Active C–terminal Fragment and Regional Homologies with Rhodopsin and Cytochrome P450", *Curr Genet* 10 879–885 (1986).

Dunphy et al., "The cdc25 Protein Contains an Intrinsic Phosphatase Activity", *Cell* 67 189–196 (1991).

Gautier et al., "Cdc 25 is a Specific Tyrosine Phosphatase that Directly Activates p34$^{cdc2}$", 67 197–211 (1991).

Gould et al., "Complementation of the Mitotic Activator, p80$^{cdc25}$, by a Human Protein–Tyrosine Phosphatase", *Science* 250 1573–1576 (1990).

Galaktionov et al., "Specific Activation of cdc25 Tyrosine Phosphatases by B–Type Cyclins: Evidence for Multipe Roles of Mitotic Cyclins", *Cell* 67 1181–1194 (1991).

Jessus et al., "Oscillation of MPF is Accompanied by Periodic Association between cdc25 and cdc2–Cyclin B", *Cell* 68 323–332 (1992).

Jimenez et al., "Complementation of Fission Yeast cdc2$^{ts}$ Mutants Identifies Two Cell Cycle Genes from Drosophila: a cdc25 Homologue and String", *Embo J* 9 3565–3571 (1990).

Kakizuka, et al., "A Mouse cdc25 Homolog is Differentially and Developmentally Expressed", *Genes & Development* 6 578–590 (1992).

Kumagai et al., "The cdc25 Protein Controls Tyrosine Dephosphorylation of the cdc2 Protein in a Cell–Free System,", *Cell* 64 903–914 (1991).

Lee et al., "cdc25$^+$Encodes a Protein Phosphatase that Dephosphorylates p34$^{cdc2}$" *Mol Biol* 3 73–84 (1992).

Millar et al., "p55$^{cdc25}$ is a Nuclear Protein Required for the Initiation of Mitosis in Human Cells" *Proc. Natl. Acad. Sci. USA* 88 10500–10504 (1991).

Millar et al., "p80$^{cdc25}$ Mitotic Inducer is the Tyrosine Phosphatase that Activates p34$^{cdc2}$ Kinase in Fission Yeast" *Embo J* 10 4301–4309 (1991).

Millar et al., "The $^{cdc25}$ M–Phase Inducer: An Unconventional Protein Phosphatase" *Cell* 68 407–410 (1992).

Moreno et al., "Clues to Action of cdc25 Protein" *Nature* 351 194 (1991).

Nagata et al., "An Additional Homolog of the Fission Yeast $^{cdc25+}$Gene Occurs in Humans and is Highly Expressed in Some Cancer Cells" *The New Biologist* 3 959–968 (1991).

Ogden et al., "Isolation of a Novel Type of Mutation in the Mitotic Control of Schizosaccharomyces Pombe whose Phenotypic Expression is Dependent on the Genetic Background and Nutritional Environment" *Curr Genet* 10 509–514 (1986).

Ohno et al., "A Yeast Gene Coding for a Putative Protein Kinase Homologous to cdc25 Suppressing Protein Kinase" *FEBS* 222 279–285 (1987).

Osmani et al., "Parallel Activation of the NIMA and p34$^{cdc2}$ Cell Cycle–Regulated Protein Kinases is Required to Initiate Mitosis in A. Nidulans" *Cell* 67 283–291 (1991).

Russell et al., "cdc25$^+$Functions as an Inducer in the Mitotic Control of Fission Yeast" *Cell* 45 145–153 (1986).

Sadhu et al, "Human Homolog of Fission Yeast cdc25 Mitotic Inducer is Predominantly Expressed om G$_2$" *Proc. Natl. Acad. Sci. USA* 87 5139–5143 (1990).

Strausfeld et al., "Dephosphorylation and Activation of a p34$^{cdc2}$/cyclin B Complex *in vitro* by Human CDC25 Protein" *Nature* 351 242–245 (1991).

Gene "Single–step purification of polypeptides expressed in Escherichia coli as fusions with glutathione S–transferase", vol.67, pp. 31–40 (1988).

*Primary Examiner*—Vasu S. Jagannathan
*Assistant Examiner*—Hyosuk Kim
*Attorney, Agent, or Firm*—Matthew P. Vincent; Beth E. Arnold; Foley, Hoag & Eliot LLP

[57] ABSTRACT

A method of identifying compounds or molecules which alter (enhance or inhibit) stimulation of kinase activity of pre-MPF and, thus, alter (enhance or inhibit) activation of MPF and entry into mitosis. The present method thus makes it possible to identify compounds or molecules which can be administered to regulate the cell cycle; such compounds are also the subject of this invention.

19 Claims, 5 Drawing Sheets

METHOD OF SCREENING FOR ANTIMITOTIC COMPOUNDS USING THE CDC25 TYROSINE PHOSPHATASE

RELATED APPLICATION

This application is a continuation of application Ser. No. 07/878,640 filed on May 5, 1992, now U.S. Pat. No. 5,294,538, which is a continuation-in-part of U.S. Ser. No. 07/793,601, entitled Novel Human cdc25 Genes, Encoded Products and Uses Thereof, by David H. Beach, filed Nov. 18, 1991, now abandoned.

FUNDING

Work described herein was funded by the National Institutes of Health (GM 69620) and the Howard Hughes Medical Institute. The United States Government has certain rights in the invention.

BACKGROUND

A universal intracellular factor, the "M phase-promoting factor" (MPF), triggers the G2/M transition of the cell cycle in all organisms. In late G2, it is present as an inactive complex of tyrosine-phosphorylated $p34^{cdc2}$ and unphosphorylated cyclin $B^{cdc13}$. In M phase, its activation as an active MPF displaying histone H1 kinase activity originates from the specific tyrosine dephosphorylation of the $p34^{cdc2}$ subunit by the tyrosine phosphatase $p80^{cdc25}$. Little is known about the signals which control or determine timing of MPF activation and entry into mitosis or about ways in which those signals can be blocked or enhanced, resulting in inhibition or facilitation of entry into mitosis. A means of identifying agents which do so would be useful, particularly because it would provide a way of controlling mitosis.

SUMMARY OF THE INVENTION

The present invention is a method of identifying compounds or molecules which alter (enhance or inhibit) stimulation of kinase activity of pre-MPF and, thus, alter (enhance or inhibit) activation of MPF and entry into mitosis. The present method thus makes it possible to identify compounds or molecules which can be administered to regulate the cell cycle; such compounds are also the subject of this invention.

In the subject method, a compound or molecule is assessed for its effect on an essential cell cycle-regulating component, cdc25 (e.g., cdc25A, cdc25B, cdc25C). As described in co-pending application U.S. Ser. No. 07/793, 601, cdc25 has been shown to be the tyrosine phosphatase which dephosphorylates cdc2, leading to MPG activation and transition from late G2 to M phase and mitosis. The present method makes use of a cell cycle-specific target and, thus, provides a highly specific mechanism-based screen for agents (compounds or molecules) which alter mitosis, particularly antimitotic agents.

In the subject method, a molecule or compound to be assessed for its ability to inhibit cdc25 tyrosine phosphatase activity is combined with cdc25 and a substrate of cdc25 tyrosine phosphatase activity. The resulting combination is maintained under conditions appropriate for cdc25 to act upon the substrate. It is then determined whether cdc25 acted upon the substrate when the compound being assessed was present; decreased activity (lack of activity or less activity than is evident when the compound is not present) indicates the compound is an inhibitor. The extent to which cdc25 acts upon the substrate in the presence of the compound is compared with the extent to which cdc25 acts on the substrate in the absence of the compound (in comparison with a control). If cdc25 activity is less in the presence of the compound, the compound is an inhibitor of cdc25.

In the subject method, a potential antimitotic agent (i.e., an agent to be assessed for an antimitotic effect) is combined with cdc25, which is either cdc25 protein or a fusion protein (e.g., recombinant $p80^{cdc}25$ present in a two-component fusion protein in which cdc25 is joined with a second component, such as glutathione-S-transferase). Subsequently, the effect of the potential antimitotic agent on the phosphatase activity of cdc25 is determined. $p80^{cdc25}$ protein has been shown, as described herein, to have p-nitrophenylphosphate phosphatase activity. Thus, the inhibitory effect of the agent being tested on cdc25 can be assessed using p-nitrophenylphosphate or inactive cyclin/ cdc2 as substrate. Results obtained (e.g., the extent of inhibition of cdc25 phosphatase activity) are particularly valuable, since they demonstrate the effect of the agent tested on a target which is particularly well suited for detecting antimitotic agents because of its direct role in controlling entry of cells into M phase.

DETAILED DESCRIPTION OF THE INVENTION

Described herein is an assay in which cdc25 tyrosine phosphatase, such as cdc25 protein or recombinant human cdc25 tyrosine phosphatase, is used as a cell cycle-specific target to screen for compounds which alter entry into mitosis (passage from late G2 into the M phase). Results of the assay (i.e., the ability of the compound being tested to inhibit cdc25) are determined by known techniques (e.g., colorimetrically, by immuno-assay techniques or by detecting enzymatic activity (e.g., histone kinase activity)). In one embodiment of the subject method, a colorimetric assay has been used, as described, to determine the ability of compounds to inhibit the cdc25 tyrosine phosphatase, which is an activator of the protein kinase MPF. As described herein, a glutathione-S-transferase/cdc25A tyrosine phosphatase fusion protein produced in Escherichia coli and purified displays a phosphatase activity towards p-nitrophenylphosphate. This fusion protein, designated GST-cdc25A, has been used to assess the inhibitory effect of compounds on cdc25 phosphatase activity. In a similar manner, as also described herein, other fusion proteins can be produced and used in the same or a similar assay format.

These fusion proteins can differ from GST-cdc25A in either or both of their components. For example, a component other than GST (e.g., maltase binding protein) can be included in the fusion protein with cdc25A. Alternatively, another member of the cdc25 family (e.g., cdc25B, cdc25C) can be the tyrosine phosphatase component. In another embodiment, cdc25 protein is used.

The present method is a simple and rapid screening test which, in one embodiment, uses a fusion protein such as recombinant p80$^{cdc25}$, assayed through its p-nitrophenylphosphate phosphatase activity, as a target to test for potential antimitotic compounds. The method has been carried out as a rapid colorimetric microtitration plate assay to test compounds currently used in cancer therapy, and a compound recognized to be a tyrosine phosphatase inhibitor. The therapeutic compounds tested did not display an ability to inhibit cdc25, in the assay as described; the reported tyrosine phosphatase inhibiter (vanadate) was shown, however, to totally inhibit cdc25. Thus, the present method has been shown to be useful in identifying compounds which inhibit an essential cell cycle-regulating component; it provides a highly specific screen for antimitotic drugs.

In one embodiment of the present method, a fusion protein which includes cdc25 is combined, under appropriate conditions, with: 1) an agent to be assessed for its effects on cdc25 and, thus, on passage from late G2 into the M phase; and 2) an appropriate cdc25 substrate, such as p-nitrophenylphosphate or inactive cdc2/cyclin B. The resulting combination is maintained for sufficient time for cdc25 to act upon the cdc25 substrate and the reaction is terminated (e.g., by gross alteration of the pH of the combination). Phosphatase activity of the combination is determined using a known technique, such as by measuring the optical density of the combination and comparing it with a predetermined standard or a control (e.g., a predetermined relationship between optical density and extent of cdc25 inhibition or a combination which includes the same components as the "test" combination except for the agent being assessed).

The fusion protein used in the present method can be produced by known genetic engineering techniques, as described in Example 1. That is, a DNA or RNA construct encoding the fusion protein is introduced into an appropriate host cell, in which the construct is expressed, thus producing the fusion protein. The fusion protein is separated (and, preferably, purified) from the host cell and used in the assay. Alternatively, the fusion protein can be produced by joining the two separately produced components. As described in Example 2, a fusion protein in which the two components are glutathione-S-transferase and human cdc25A has been produced and used in the subject method.

In a second embodiment, cdc25 protein, such as cdc25A, cdc25B or cdc25C protein, can be used in the subject method. In this embodiment, cyclin/cdc2 can be used as the cdc25 substrate; an agent to be tested is combined with cdc25 protein and cyclin/cdc2 and the tyrosine phosphatase activity of cdc25 is assessed, as described above. Results are compared with a predetermined standard or with a control. (See Example 1)

The cdc25 substrate used can be any synthetic or naturally-occurring substance toward which cdc25 demonstrates phosphatase activity. In the embodiment described herein, the cdc25A substrate used is p-nitrophenylphosphate. Other substrates which can be used include peptides that mimic the site of cdc2 phosphorylation or the full inactive cdc2/cyclinB pre-enzyme complex. Others can be identified by using known methods of determining phosphatase activity.

Agents to be tested for their ability to alter cdc25 tyrosine phosphatase activity can be those produced by bacteria, yeast or other organism or those produced chemically. The compounds tested as described herein included 15 drugs currently used in cancer therapy (see the Table) and vanadate, a recognized tyrosine phosphatase inhibitor. The 15 therapeutic agents showed no inhibitory activity. In contrast, vanadate was shown to totally inhibit GST-cdc25A phosphatase. The present method is useful to identify agents potentially effective as antiproliferative agents and agents which are useful in treating or preventing inflammation or psoriasis, etc.

Alternatively, the present method can be used to identify compounds which enhance cdc25 tyrosine phosphatase activity.

The present invention will now be illustrated by the following examples, which are not intended to be limiting in any way.

Materials and Methods

Chemicals sodium fluoride, sodium orthovanadate, nitrophenol, cis-platinum, isopropyl β-D-thiogalactopyranoside (IPTG), 1-methyladenine, dithiothreitol (DDT), EGTA, EDTA, MOPS, β-glycerophosphate, leupeptin, aprotinin, soybean trypsin inhibitor, benzamidine, histone H1 (type III-S), CNBr-activated sepharose 4B, glutathione-agarose (G 4510), glutathione (G 4251), nonidet P40 (NP40), Tris, LB Broth base, were obtained from Boehringer-Mannheim, p-nitrophenylphosphate (p-NPP) (disodium salt hexahydrate, ref. 12.886.82) was from Janssen Chimica.

[γ-$^{32}$P]-ATP (PB 168) and $^{125}$I]-protein A (IM 144) were obtained from Amersham.

G1 anti-p34$^{cdc2}$ antibodies and anti-p80$^{cdc25}$ antibodies (directed against the cdc25C phosphatase peptide H$_2$N-QEGERQLREQIALLVKDMS-COOH) were kindly provided by Dr. G. Draetta (Heidelberg), anti-cyclin B$^{cdc13}$ (starfish) antibodies were generously donated by Dr. T. Kishimoto (Tokyo), anti-phosphotyrosine antibodies were generously given by Dr. J. Y. J. Wang (La Jolla), antibodies against H$_2$N-VEKIGEGTYGVVYKARHKLS-COOH (a p34$^{cdc2}$ peptide containing the regulatory threonine-14 and tyrosine-15 residues) were kindly provided by Dr. L. Tung (Philadelphia). This last antibody does not recognize tyrosine-phosphorylated p34$^{cdc2}$ but only tyrosine-dephosphorylated p34$^{cdc2}$.

Buffers

Oocyte homogenization buffer contained 60 mM β-glycerophosphate, 15 mM p-NPP, 20 mM MOPS pH 7.2, 15 mM EGTA, 15 mM MgCl$_2$, 1 mM DTT, 0.1 mM sodium vanadate, 0.1 mM sodium fluoride, 10 μg leupeptin/ml, 10 μg aprotinin/ml, 10 μg soybean trypsin inhibitor/ml, 100 μM benzamidine. This buffer had previously been shown to stabilize the starfish meiotic oocyte M phase-specific histone H1 kinase (Pelech, S. L. et al., *Biochemistry* 26:7960–7968 (1987)).

Bead buffer contained 50 mM Tris pH 7.4, 5 mM NaF, 250 mM NaCl, 5 mM EDTA, 5 mM EGTA, 0.1% NP40, 10 μg leupeptin/ml, 10 μg aprotinin/ml, 10 μg soybean trypsin inhibitor/ml and 100 μM benzamidine.

Tris-Buffered Saline (TBS) contained 50 mM Tris pH 7.4, 150 mM NaCl.

Phosphate-Buffered Saline (PBS) contained 9.6 mM phosphate, 2.7 mM KCl, 140 mM NaCl.

Lysis buffer contained 1% NP40, 1 mM EDTA, 1 mM DTT, 10 μg leupeptin/ml, 10 μg aprotinin/ml, 10 μg soybean trypsin inhibitor/ml and 100 μM benzamidine/ml in PBS.

Tris buffer A contained 50 mM Tris pH 8.0, 50 mM NaCl, 1 mM EDTA, 1 mM DTT.

Elution buffer contained 10 mM glutathione in Tris buffer A.

Preparation of G2 and M Phase Oocytes

G2 and M phase oocytes were prepared as follows: Gonads were removed from mature starfish (*Marthasterias glacialis*), collected in Northern Brittany. They were either directly frozen in liquid nitrogen and kept at −80° C. (G2 oocytes) or incubated with 10 μM 1-methyladenine in natural seawater for 10 min (M. oocytes). By that time all the oocytes had entered the M phase, although they were still in the gonads. These were then removed from the incubation medium, rapidly blotted on filter paper, directly frozen in liquid nitrogen and kept at −80° C.

Transfer buffer contained 39 mM glycine, 48 mM Tris, 0.37% SDS, 20% methanol.

Bacterial Growth and cdc25A Induction

An *E. coli* strain (BL 21(DE3)) containing a plasmid encoding the genes fusion construct of glutathione-S-transferase (GST) and human cdc25A under the control of IPTG was used (Galaktionov, K. and D. Beach, *Cell* 67:1181–1194 (1991)). *E. coli* were first grown overnight at 37° C. in the presence of 100 μg ampicillin/ml LB medium. Four ml of this preculture were inoculated/liter of LB containing 100 μg ampicillin/ml. Incubation was pursued at 30° C. until the culture O.D. at 500 nm had reached a value between 0.8 and 1.00 (about 4–5 hrs). At this moment, 0.4 mM IPTG was added and the culture incubated at 25° C. for at least 7 hrs. Cells were then harvested by a 3000 g centrifugation for 15 min at 4° C. Pellets were kept frozen at −80° C. until extraction.

EXAMPLE 1 p80$^{cdc25}$ Controls p34$^{cdc2}$/cyclin B Activation

Figure 1:
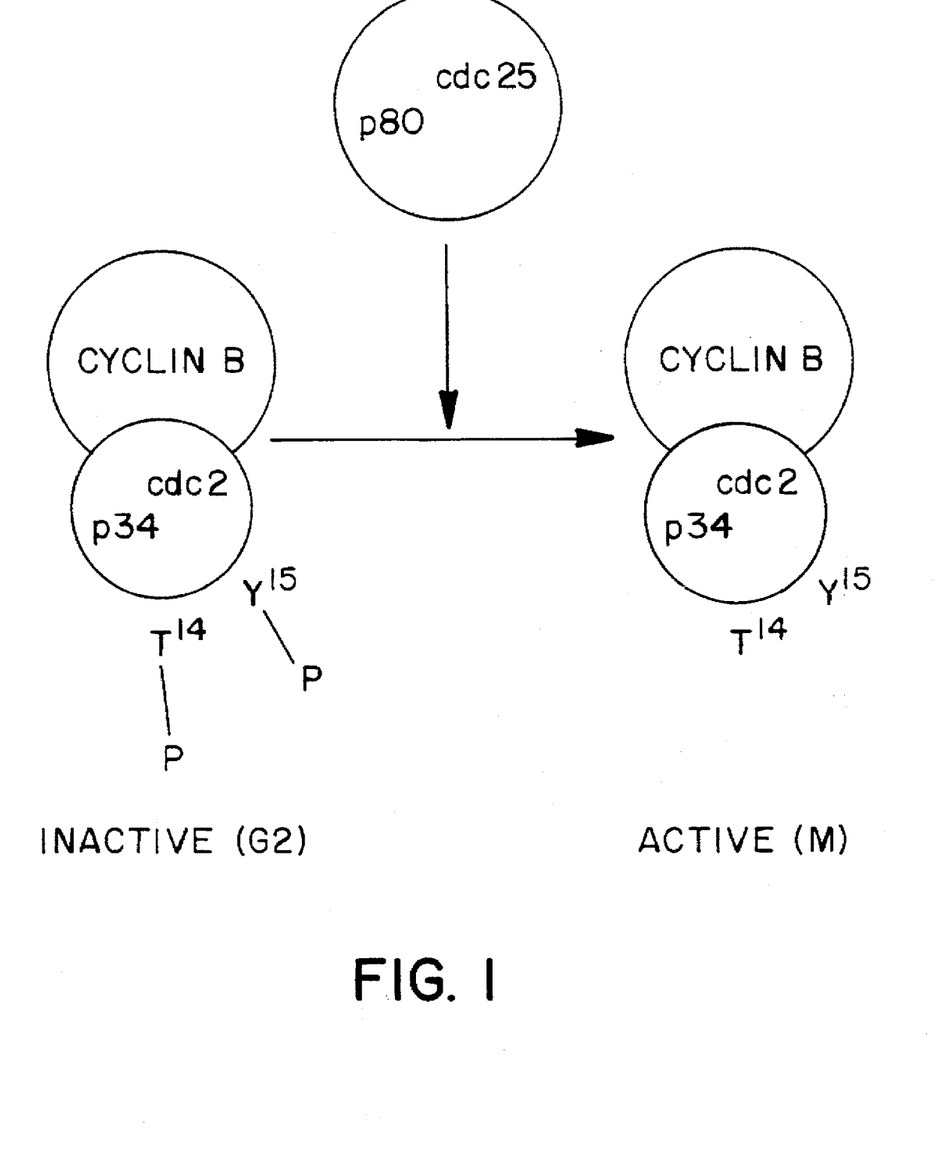
FIG. 1 is a schematic representation of the control by $p80^{cdc25}$ of activtion of inactive pre-MPF(G2) to active MPF (M phase).

Inactive pre-MPF (G2) is constituted of cyclin B and p34$^{cdc2}$ phosphorylated on its threonine-14 and tyrosine-15 residues. p80$^{cdc25}$ is the phosphatase which dephosphorylates the tyrosine-15 residue, and possible threonine-14. Its action leads to activation of the p34$^{cdc2}$/cyclin B$^{cdc}$13 kinase responsible for induction of the G2/M transition. The interaction of these components and activation of inactive pre-MPF (G2) is represented in FIG. 1. An agent to be tested for its ability to alter stimulation of kinase activity is combined with the inactive pre-MPF (G2) and the effects, if any, are determined. If an agent tested is an inhibitor, the inactive pre-MPF will not be activated.

EXAMPLE 2

Production and Purification of GST-cdc25A Phosphatase

A fusion construct between the glutathione-S-transferase (GST) gene and human cdc25A was built in a plasmid vector (Galaktionov, K. and D. Beach, *Cell* 67:1181–1194 (1991)). Transfected and expressed in *E. coli*, it produces large amounts of the corresponding fusion protein which can be purified by affinity chromatography on glutathione-agarose beads. The protocols of production, purification and assay of the GST-cdc25A phosphatase is described in detail below. Production involves culture of recombinant *E. coli* and classical induction of GST-cdc25A expression by IPTG. One-step affinity-chromatography on glutathione-agarose allows the purification of the GST-cdc25A phosphatase. The optimum ratio of bacterial extract volume/ glutathioneagarose volume was found to be 6–10 to 1. Glutathione-agarose can be easily recycled. GST-cdc25A was either preserved as the bacterial pellet (very stable), the supernatant of the centrifuged bacterial extract or after affinity-purification and in the presence of 40% glycerol (final volume).

The bacterial pellet was disrupted by sonication in lysis buffer at 4° C. The homogenate was centrifuged for 30 min at 4° C. at 100,000 g; the supernatant was recentrifuged under similar conditions; the final supernatant was then immediately mixed and rotated with glutathione-agarose beads (equilibrated with lysis buffer) for 30 min at 4° C. (6–10 volumes of supernatant/1 volume of packed beads). The glutathione-agarose beads were washed three times with 10 volumes of lysis buffer, followed by four washes with 10 volumes of Tris buffer A. Elution of the fusion protein was induced by 3–4 successive washes with 10 mM glutathione in Tris buffer A. The efficiency of the elution was monitored by a phosphatase assay. Active fractions were pooled and used directly or supplemented with 40% glycerol prior to storage 15 80° C.

Glutathione-agarose beads can be recycled by a wash with 1M NaCl, followed by equilibration with lysis buffer.

EXAMPLE 3

Assay of the GST-cdc25A Phosphatase Activity Towards p-Nitrophenylphosphate

Figure 3A:
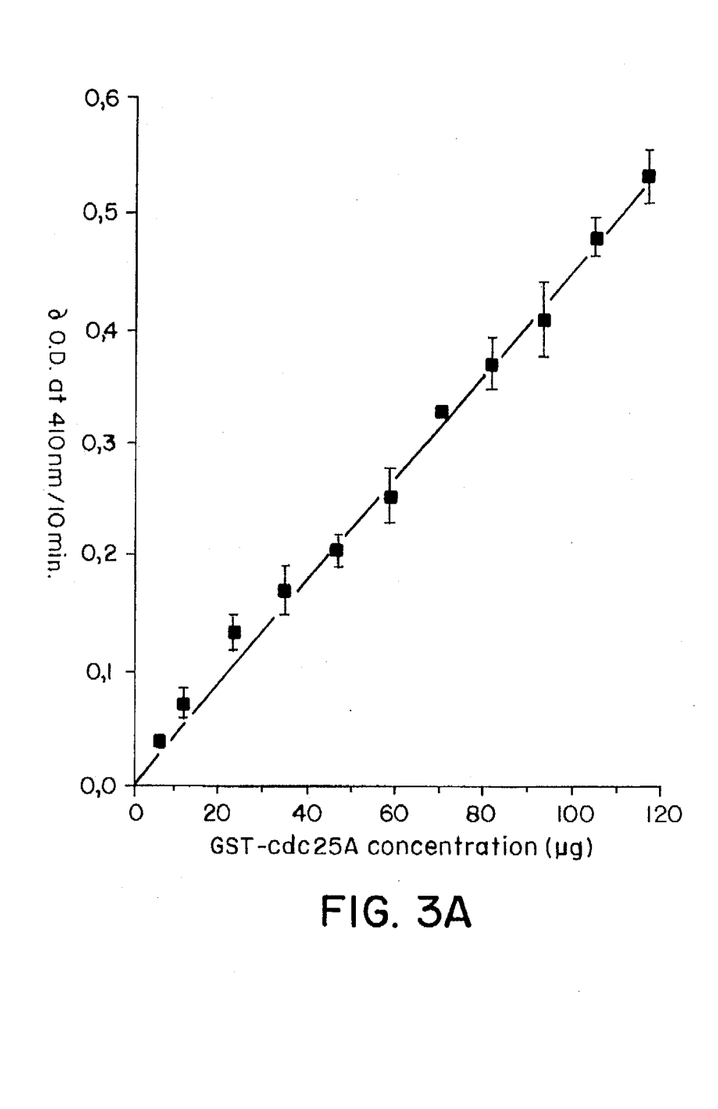
FIGS. 3A and 3B is a graphic representation of GST-cdc25-pNPP phosphatase activity as a function of GST-cdc25A concentration (FIG. 3A) and as a function of duration of assay (FIG. 3B).
Figure 3B:
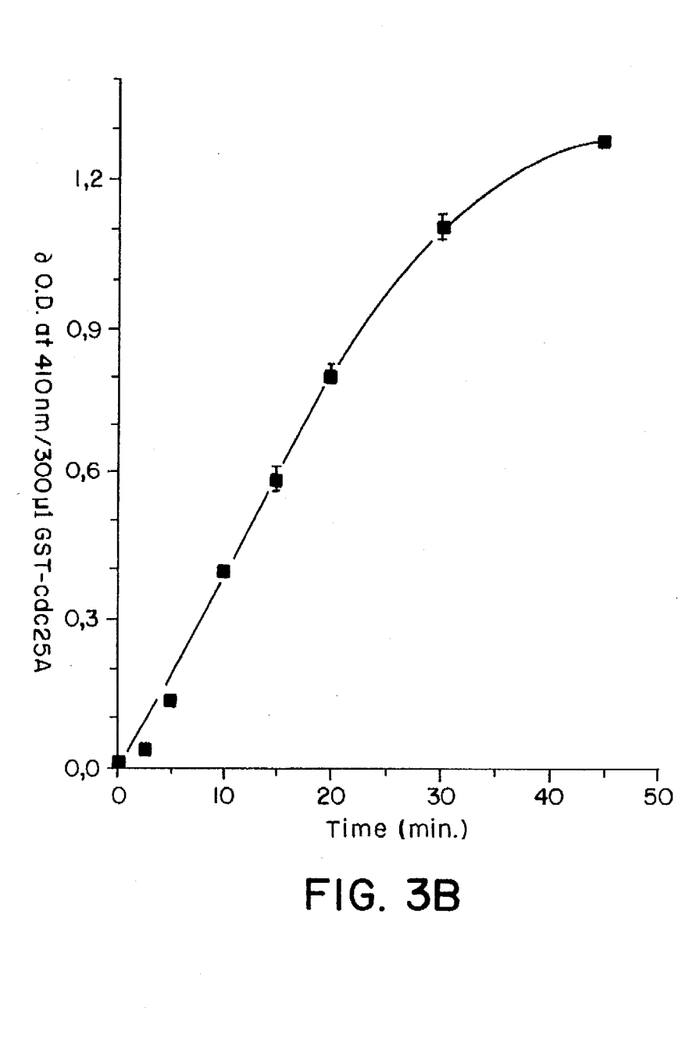
Figure 4A:
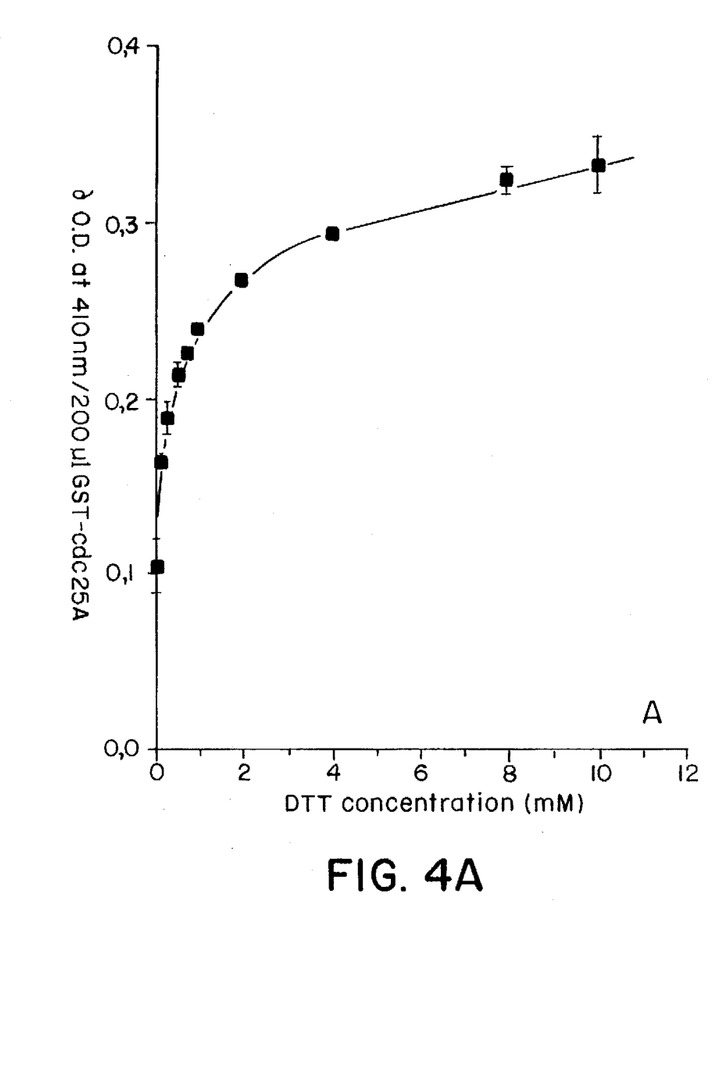
FIGS. 4A and 4B is a graphic representation of GST-cdc25a activity as a function of DTT concentration (FIG. 4A) and p-NPP concentration (FIG. 4B).
Figure 4B:
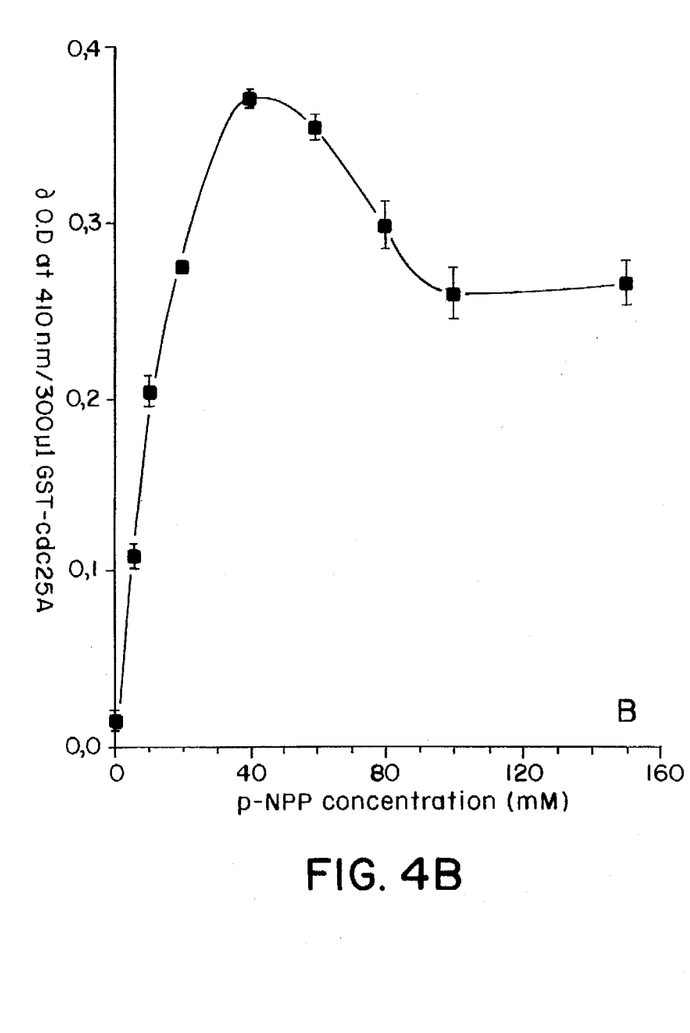

GST-cdc25A phosphatase activity can be very conveniently assayed using the chromogenic substrate p-nitrophenylphosphate (p-NPP). Optimal conditions for several parameters were determined with a one ml assay, as described below. Results are represented graphically in the figures: amount of GST-cdc25A phosphatase (FIG. 3A), duration of assay (FIG. 3B), DTT concentration (FIG. 4A), p-NPP concentration (FIG. 4B).

One ml assay: 100 μl of GST-cdc25A protein (diluted to an activity of ∂ OD 410 nm=0.3/10 min) were mixed with 100 μl mM DTT (in Tris buffer A) and 700 μl of Tris buffer A. The assay was initiated by addition of 100 μl 500 mM p-NPP (in Tris buffer A). After 10 min incubation at 37° C., the assay was terminated by addition of 40 μl 5N NaOH and transfer of the tubes to 4° C. Absorbance at 410 nm was then measured and blank values (no GST-cdc25A protein but 10 min incubation) were subtracted.

This assay was then scaled down to 200 μl and conducted semi-automatically in 96-wells microtitration plates, as described in detail below. Each well is filled with 20 μl GST-cdc25A phosphatase, 140 μl Tris buffer A, 20 μl 100 mM DTT (in Tris buffer A); after 15 min equilibration at 37° C., reaction is initiated by addition of 20 μl 500 mM p-NPP (in Tris buffer A). After 60 min incubation absorbance at 405 nm is monitored in a microplate reader; blank values (no GST-cdc25A added) is subtracted.

Microtitration plate assay: 20 μl of GST-cdc25A protein (diluted to an activity of ∂ O.D.405 nm=0.2–0.3/60 min) were mixed with 20 μl 100 mM DTT (in Tris buffer A) and 140 μl of Tris buffer A, in 96-wells microtitration plates (Corning). The plates were preincubated at 37° C. for 15 min in a Denley Wellwarm 1 microplate incubator. The assays were initiated by addition of 20 µl of 500 mM p-NPP (in Tris buffer A). After 60 min incubation at 37° C. absorbance at 405 nm was measured in a bioRad microplate reader. Blank values (no CST-cdc25A protein added) were automatically substracted.

EXAMPLE 4

Figure 2A:
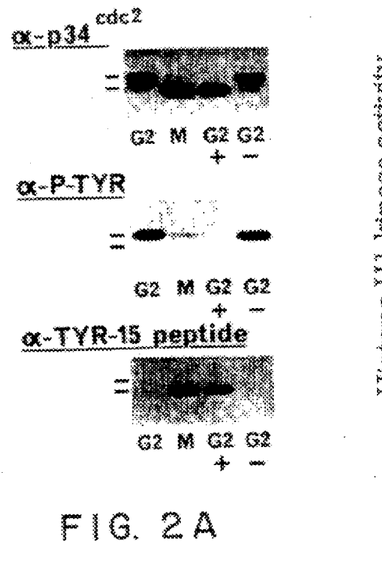
FIGS. 2A and 2B is evidence that the GST-cdc25a fusion protein dephosphorylates $p34^{cdc2}$ and activates the M phase-specific H1 kinase (MPF).
Figure 2B:
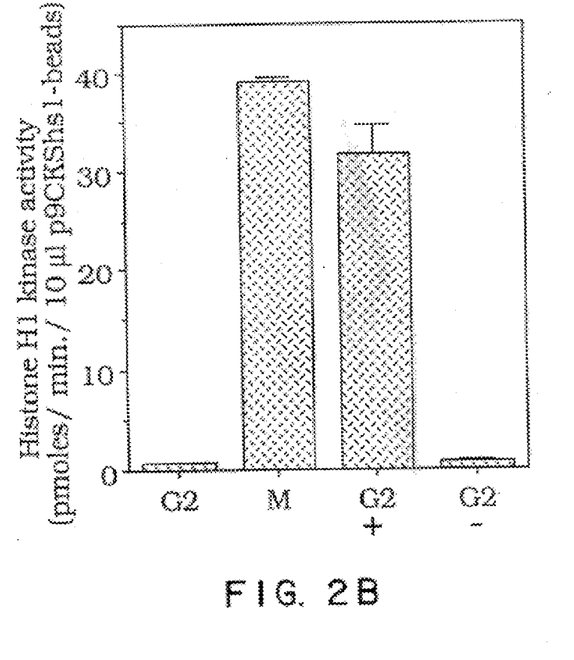

Tyrosine Dephosphorylation and Activation of the $p34^{cdc2}$/cyclin $B^{cdc13}$ Kinase by the Fusion Protein GST-cdc25A The ability of the GST-cdc25A fusion protein to dephosphorylate and activate the $p34^{cdc2}$/cyclin $B^{cdc13}$ kinase was demonstrated. $p34^{cdc2}$/cyclin $B^{cdc13}$ complex from G2-arrested starfish oocytes was immobilized on $p9^{CKShs1}$ agarose: it is constituted of tyrosine-phosphorylated $p34^{cdc2}$ and cyclin $B^{cdc13}$ (Arion, L. et al., *Eur. J. Biochem.:* (1992); Pondaven, P. et al., *Genes and Development* 4:9–17 (1990)). Treatment with purified GST-cdc25A protein induced almost complete tyrosine dephosphorylation of $p34^{cdc2}$ as shown (FIG. 2, left) by the $p34^{cdc2}$ mobility shift (upper panel), the loss of cross-reactivity with anti-phosphotyrosine antibodies (middle panel) and the appearance of cross-reactivity with an antibody directed against a $p34^{cdc2}$ peptide comprising the tyrosine-15 residue (lower panel). In addition, this tyrosine dephosphorylation lead to histone H1 kinase activation to a level close to that found in M phase oocytes (FIG. 2, right). By these criteria, the GST-cdc25A fusion protein appears to display all the physiological enzymatic activity of cellular $p80^{cdc}25$.

Assay of $p34^{cdc2}$/Cyclin $B^{cdc13}$ Kinase Activity

Oocyte extracts were prepared by homogenization of 1 g of G2 or M phase gonads per 2 ml homogenization buffer. After centrifugation for 10 min at 14,000 g at 4° C., the supernatants were loaded on $p9^{CKShs1}$-sepharose beads prepared as described in (Azzi, L. et al., *Eur. J. Biochem.:* in press (1992)) (400 µl supernatant/10 µl $p9^{CKShs1}$-beads). [DB: NEED THE PREPARATION METHOD DESCRIBED IN Azzi, SINCE IT'S NOT PUBLISHED] The tubes were kept under constant rotation at 4° C. for 30 min. After a brief centrifugation at 10,000 g and removal of the supernatant, the beads were washed three times with bead buffer and eventually exposed to purified GST-cdc25A phosphatase prior to H1 kinase assay or to immunoblotting analysis.

Histone H1 kinase assays were performed by incubation of 10 µl of packed $p9^{CKShs1}$-beads (loaded with G2 or M phase extrCTS) for 10 min at 30° C. with 15 µM [γ-32P] ATP (3,000 Ci/mmol; 1 mCi/ml) in the presence of 1 mg histone II1/ml in a final volume of 40 µl. Assays were terminated by transferring the tube onto ice. After a brief centrifugation at 10,000 g, 30 µl aliquots of supernatant were spotted onto 2.5×3 cm pieces of Whatman P81 phosphocellulose paper, and after 20 sec, the filters were washed five times (for at least 5 min each time) in a solution of 10 ml lphosphoric acid/liter of water. The wet filters were transferred into 6 ml plastic scintillation vials, 5 ml ACS (Amersham) scintillation fluid was added and the radioactivity of the samples measured in a Packard counter.

Electrophoresis and Western Blotting

Proteins bound to p9CKShs1-sepharose beads were recovered with 50 µl 2X Laemmli sample buffer. Samples were run in 10% SDS/polyacrylamide gels. Proteins were stained with Coomassie Blue or transferred to 0.1 µm nitrocellulose sheets (Schleicher & Schull) in a Milliblot/SDE system (Millipore) for 30 min at 2.5 mA/cm² in transfer buffer. The filters were subsequently blocked with TBS containing 3% bovine serum albumin for 1 hr at room temperature. The filters were then incubated overnight at 4° C. with g1 anti-p34CDC2 antibodies (1:1000 dilution), anti-p34$^{cdc2}$ peptide antibodies (1:500 dilution) or anti-phosphotyrosine antibodies (1 µg/ml). After four washes of 15 min each with TBS containing 0.2% NP40, the filters were treated with 1 µCi $^{125}$I-protein A (30 mCi/mg) in 3% bovine serum albumin in TBS for 2 hr at room temperature. After four 15 min washes with 0.2% NP40 in TBS, the filters were exposed overnight to hyperfilm MP (Amersham).

EXAMPLE 5

Detection of Inhibitors of Purified GST-cdc25A Phosphatase

Figure 5:
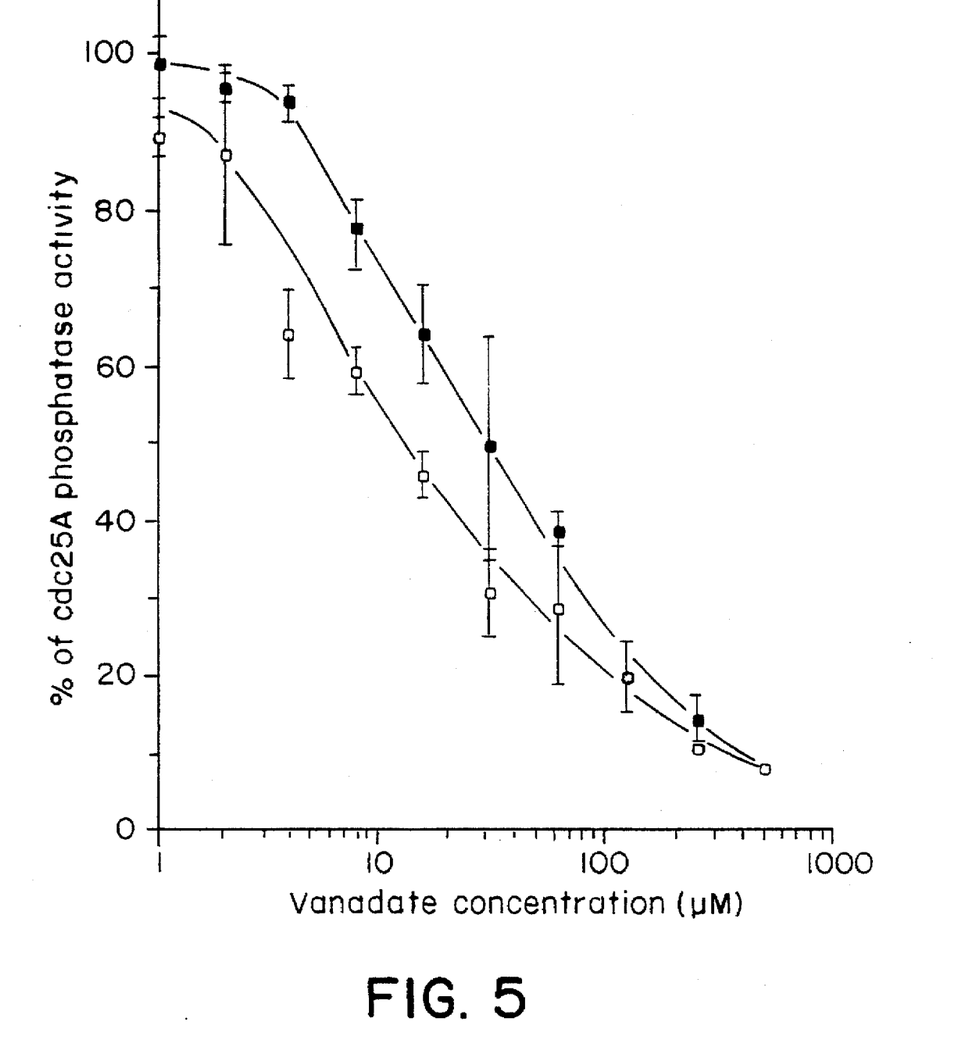
FIG. 5 is a graphic representation of the inhibitory effect of sodium orthovanadate on GST-cdc25A tyrosine phosphatase, in which phosphatase activity is expressed as % of activity in the absence of vanadate (mean ±SD).

In a first series of experiments various antimitotic compounds currently used in cancer therapy were tested as potential inhibitors of the phosphatase (the Table). Most of them are reported to act as DNA damaging agents, as DNA intercalators, as topoisomerase 2 inhibitors or as compounds interfering with spindle microtubles. None of them displayed GST-cdc25A phosphatase inhibitory activity. As a positive control we then tested vanadate, a reported inhibitor of tyrosine phosphatases (Gordon, J. A., *Methods in Enzymology* pp.477–482 (1991)). This compound totally inhibites the GST-cdc25A phosphatase at concentrations above 500 µM (FIG. 5; $I_{50}$=20 µM).

TABLE

ANTIMITOTIC COMPOUNDS TESTED AS POTENTIAL INHIBITORS of $p80^{cdc25A}$

| Compounds | Range of Concentration Tested |
| --- | --- |
| Actinomycin D | 0.1–100 µg/ml |
| BCNU | 0.1–100 µg/ml |
| Carboplatin | 0.1–100 µg/ml |
| Chlormethine | 0.1–100 µg/ml |
| Cis-platinum | 0.1–100 µg/ml |
| Cyclophosphamide | 0.1–100 µg/ml |
| Dacarbazine | 0.1–100 µg/ml |
| Doxorubicin | 0.1–100 µg/ml |
| Etoposide | 0.1–100 µg/ml |
| Fluoro-uracil | 0.1–100 µg/ml |
| Girolline | 0.36–360 µg/ml |
| Methotrexate | 0.1–100 µg/ml |
| Novobiocin | 0.1–100 µg/ml |
| Vinblastine | 0.1–100 µg/ml |
| Vincristine | 0.1–100 µg/ml |

None of the compounds exhibited more than 5–10% inhibitory activity on the enzyme over the indicated range of concentration.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a compound which is an inhibitor of a cdc25 tyrosine phosphatase activity, comprising the steps of:
   a) combining:
      1) a test compound to be assessed;
      2) a cdc25 phosphatase selected from the group consisting of cdc25A and cdc25B; and
      3) a substrate of the cdc25 phosphatase;

b) maintaining the combination produced in (a) under conditions appropriate for the cdc25 phosphatase to act upon the substrate; and c) determining the extent to which the cdc25 phosphatase present in the combination produced in (a) acts upon the substrate, relative to a control, the control comprising the cdc25 phosphatase and the substrate but lacking the test compound, wherein, if the cdc25 phosphatase present in the combination produced in (a) acts upon the substrate to a lesser extent than the cdc25 phosphatase present in the control, the test compound is an inhibitor of a cdc25 tyrosine phosphatase.

2. The method of claim 1, wherein the cdc25 phosphatase is a mammalian cdc25 phosphatase.

3. The method of claim 1, wherein the cdc25 phosphatase is a component of a fusion protein.

4. The method of claim 3, wherein the fusion protein is a glutathione-S-transferase/cdc25 tyrosine phosphatase fusion protein.

5. A method of identifying a compound which is an inhibitor of a cdc25 tyrosine phosphatase activity, comprising the steps of:

a) combining:
1) a fusion protein comprising a cdc25 tyrosine phosphatase selected from the group consisting of cdc25A and cdc25B;
2) a cdc25 tyrosine phosphatase substrate, other than an active cdc2 kinase; and
3) a test compound, thereby producing a combination;

b) maintaining the combination produced in (a) under conditions appropriate for the cdc25 tyrosine phosphatase to act upon the cdc25 tyrosine phosphatase substrate;

c) determining the extent to which the cdc25 tyrosine phosphatase in the fusion protein acts upon the cdc25 tyrosine phosphatase substrate in the combination produced in (a);

d) comparing the result of (c) with the extent to which the cdc25 tyrosine phosphatase in the fusion protein acts upon the cdc25 tyrosine phosphatase substrate of (a)(2) in the absence of the test compound, wherein if the extent to which the cdc25 tyrosine phosphatase acts upon the cdc25 tyrosine phosphatase substrate in the presence of the test compound is less than the extent to which the cdc25 tyrosine phosphatase acts upon the cdc25 tyrosine phosphatase substrate in the absence of the test compound, the test compound is an inhibitor.

6. A method of identifying a compound which is an inhibitor of a cdc25 tyrosine phosphatase activity, comprising the steps of:

a) combining:
i) a test compound to be assessed;
ii) a protein having a tyrosine phosphatase activity of a cdc25 phosphatase selected from the group consisting of a cdc25A phosphatase and a cdc25B phosphatase; and
iii) a synthetic substrate of the tyrosine phosphatase activity comprising a colorimetric label which is detectable when the substrate is acted upon by the tyrosine phosphatase activity;

b) maintaining the combination produced in (a) under conditions appropriate for the tyrosine phosphatase activity to act upon the substrate; and c) determining, by colorimetric assay, the extent to which the tyrosine phosphatase activity present in the combination produced in (a) acts upon the substrate, relative to a control, the control comprising the tyrosine phosphatase activity and the substrate but lacking the test compound, wherein if the tyrosine phosphatase activity present in the combination produced in (a) acts upon the substrate to a lesser extent than the tyrosine phosphatase activity acts upon the substrate in the control, the test compound is an inhibitor of cdc25 tyrosine phosphatase activity.

7. The method of claim 6, wherein the cdc25 phosphatase is a mammalian cdc25 phosphatase.

8. The method of claim 6, wherein the cdc25 phosphatase is a component of a fusion protein.

9. The method of claim 8, wherein the cdc25 phosphatase is a cdc25-glutathione-S-transferase fusion protein.

10. A method of identifying a compound which is an inhibitor of a human cdc25 tyrosine phosphatase activity, comprising the steps of:

a) combining:
i) a test compound to be assessed;
ii) a cdc25 phosphatase from a human source, which cdc25 phosphatase is selected from the group consisting of a cdc25A phosphatase and a cdc25B phosphatase; and
iii) a synthetic substrate of the cdc25 phosphatase comprising a colorimetric label which is detectable when the substrate is acted upon by the cdc25 phosphatase;

b) maintaining the combination produced in (a) under conditions appropriate for the cdc25 phosphatase to act upon the substrate; and c) determining, by colorimetric assay, an extent to which the cdc25 phosphatase present in the combination produced in (a) acts upon the substrate, relative to a control, the control comprising cdc25 phosphatase and the substrate but lacks the test compound, wherein if the cdc25 phosphatase present in the combination produced in (a) acts upon the substrate to a lesser extent than cdc25 phosphatase acts upon the substrate in the control, the test compound is an inhibitor of human cdc25 tyrosine phosphatase activity.

11. A method of identifying a compound which is a potential inhibitor of a cdc25 phosphatase activity, comprising the steps of:

a) combining:
1) a test compound;
2) a recombinant cdc25 phosphatase encoded by a mammalian cdc25 gene selected from the group consisting of cdc25A and cdc25B; and
3) a substrate of the cdc25 phosphatase;

b) maintaining the combination produced in (a) under conditions appropriate for the cdc25 phosphatase to enzymatically convert the substrate to product; and c) comparing the rate of substrate conversion in the presence of the compound to a control sample comprising the cdc25 phosphatase and the substrate but no test compound, wherein a decrease in the rate of substrate conversion in the presence of the compound, relative to the control sample, indicates a the compound is a potential inhibitor of the cdc25 phosphatase.

12. The method of any of claims 1, 5, 6, 10, or 11, wherein the cdc25 phosphatase is a cdc25A phosphatase.

13. The method of any of claims 1, 11, 6, 10 or 11, wherein the cdc25 phosphatase is a cdc25B phosphatase.

14. The method of any of claims 1, 6 or 10, wherein the cdc25 phosphatase is provided as a purified protein.

15. The method of any of claims 1, 6 or 10, wherein the cdc25 phosphatase is provided as a recombinant protein.

16. The method of any of claims 2, 5 or 7, wherein the cdc25 phosphatase is a human cdc25.

17. The method of claim 11, wherein the mammalian cdc25 gene is a human cdc25 gene.

18. The method of any of claims 1, 5 or 11, wherein the substrate of the cdc25 phosphatase provides a colorimetric indicator of phosphatase activity.

19. The method of claim 6, wherein the substrate is a p-nitrophenylphosphate.

* * * * *